United States Patent [19]

Parker et al.

[11] Patent Number: 5,271,927

[45] Date of Patent: Dec. 21, 1993

[54] ANTIBODY CONJUGATES WITH MACROCYCLIC LIGANDS

[75] Inventors: David Parker, Durham; Thomas A. Millican, Maidenhead, both of United Kingdom

[73] Assignee: Celltech Limited, Berkshire, United Kingdom

[21] Appl. No.: 33,461

[22] Filed: Mar. 18, 1993

Related U.S. Application Data

[60] Continuation of Ser. No. 772,777, Oct. 7, 1991, abandoned, which is a division of Ser. No. 132,955, Dec. 14, 1987, Pat. No. 5,087,696.

[30] Foreign Application Priority Data

Feb. 13, 1986 [GB] United Kingdom ............... 8603537

[51] Int. Cl.$^5$ ............... A61K 39/395; A61K 47/22; A61K 47/16; A61K 47/06
[52] U.S. Cl. ................................ 424/9; 530/391.1; 530/391.3; 530/391.5; 424/85.91; 540/465; 540/467; 540/469; 540/470; 540/471; 540/473; 540/474
[58] Field of Search ............... 540/465, 467, 469, 470, 540/471, 473, 474; 424/85.91, 9; 530/387.1, 388.1, 391.1, 391.3, 391.5

[56] References Cited

U.S. PATENT DOCUMENTS

| | | | |
|---|---|---|---|
| 4,174,319 | 11/1979 | Kobuke ................... | 260/239 |
| 4,174,428 | 11/1979 | Tabushi et al. ........... | 540/474 |
| 4,432,907 | 2/1984 | Wieder et al. ............ | 436/500 |
| 4,472,509 | 9/1984 | Gansow et al. ........... | 436/548 |
| 4,659,839 | 4/1987 | Nicolotti et al. .......... | 548/546 |
| 4,671,958 | 7/1987 | Rodwell et al. .......... | 514/2 |
| 4,678,667 | 7/1987 | Meares .................... | 424/85 |
| 4,877,600 | 10/1989 | Bonnemain et al. ...... | 257/2 |
| 4,885,363 | 12/1989 | Tweedle et al. .......... | 540/465 |
| 5,049,667 | 9/1991 | Schaefer et al. .......... | 540/474 |
| 5,053,503 | 10/1991 | Dean et al. ............... | 540/474 |
| 5,087,696 | 2/1992 | Parker et al. ............. | 540/465 |

FOREIGN PATENT DOCUMENTS

| | | |
|---|---|---|
| 76267/87 | 2/1988 | Australia . |
| 0173629 | 8/1985 | European Pat. Off. . |
| 0188256 | 7/1986 | European Pat. Off. . |
| 0232751 | 8/1987 | European Pat. Off. ............. 540/474 |
| 88/08422 | 11/1988 | PCT Int'l Appl. . |
| 89/01476 | 2/1989 | PCT Int'l Appl. . |

OTHER PUBLICATIONS

Khaw et al., Science, 209, 295 (1980).
Krejcarek et al., Biochem. Biophys. Res. Comm., 77, 581 (1977).
Childs, R. L. and Hnatowich, D. J., J. Nuc. Med. 26, 293 (1985).
Stetter, H., et al., Angew. Chem. Int. Ed. Engl., 15 686 (1976).
Loncin, J. F., et al., Inorg. Chem., 25, 2646 (1986).
Moi, C. F., et al. J. Am. Chem. Soc., 110, 6266 (1988).
Tweedle, M. F., et al., J. Nuc. Med., 28, 705 (1988).
Goodwin, C. H., et al., J. Nuc. Med., 27, 959 (1986).
Paik, C. H., et al., J. Nuc. Med., 28, 572 (1987).
Paik, C. H., et al., J. Nuc. Med., 29, 889 (1988).
Haseman, C. F., et al., Eur. J. Nuc. Med., 12, 455 (1986).
Parker et al., Pure & Appl. Chem., vol. 61, No. 9, 1637-1641 (1989).
Craig et al., J. Chem. Soc. Chem. Commun. (1989), pp. 794-796.
Cox et al., J. Chem. Soc. Chem. Commun. (1989), pp. 797-798.
Paik et al., J. Nucl. Sci., vol. 30, No. 10, pp. 1693-1701 (Oct. 1989).
Paik et al., Nucl., Med. Biol., vol. 16, No. 5, pp. 475-481 (1989).
Deshpande et al., Nucl. Med. Biol., vol. 16, No. 6, pp. 587-597 (1989).
Deshpande et al., The Journal of Nuclear Medicine. "Copper-67-Labeled Monoclonal Antibody Lym-1, A Potential Radio-pharmaceutical for Cancer Therapy: Labeling and Biodistribution in RAJI Tumored Mice", vol. 29, No. 2, pp. 217-225 (Feb. 1988).
Franz, J., et al., Abstract from Journal of Nuclear Medicine, Abstract No. 553, vol. 26, No. 5 (May 1985).
Franz et al., poster exhibited at 32nd Annual Meeting of the Society of Nuclear Medicine prior to May 1985.
Meares, Claude F., "Protein Tailoring for Food and Medicine Uses edited by R. E. Feeny et al., Attaching Metal Ions to Antibodies", pp. 339-352 (1986).
Goodwin, D. A., et al., Abstract of "In Complex of a New Macrocyclic Bifunctional Chelator TETA", presented at European Nuclear Medicine Congress Meeting at Barbican, London, Sep. 3-6 (1985).
Meares et al., Int. J. Cancer Suppl., 2, 99-102 (1988).
Meares et al., Br. J. Cancer, 62, 21-26 (1990).
Gransow et al., ACS Symposium Series, No. 241, "Generator Produced Bi-212" (1984).
Moi et al., Anal. Biochem., 148, 249-253 (1985).

Primary Examiner—Y. Christina Chan
Assistant Examiner—Phillip Gambel

[57] ABSTRACT

The conjugation of antibodies to a macrocyclic conjugate compound wherein the conjugate compound has the structure (I), wherein $R^1$ is $-(CH_2)_p-R^6-CH_2)_q-$ where p and q are the same or different and are 0, 1 or 2, and $-R^6-$ is $-((CH_2)_n-$, where n is 0 or 1, $-NH-$, $-O-$, $-S-$ or (II), $R^1$ optionally being alkyl substituted, provided that neither p nor q is 0 unless $R^6$ is $-CH_2-$; $R^2$ are $-CH_2CH_2-$ or $-CH_2CH_2CH_2-$, optionally alkyl, alkoxyalkyl or hydroxyalkyl substituted; $R^3$ are the same or different and are $-H$, alkyl, hydroxyalkyl, alkoxyalkyl, carboxyalkyl, carboxyalkyl ester, phosphate, sulphonate or phosphonate; $R^4$ is one of the compounds of formula (III) optionally alkyl substituted, wherein $R^7$ is $-H$, alkyl, hydroxyalkyl, or alkoxyalkyl provided that when $R^4$ is (III d), $R^3$ is not carboxyalkyl, $R^5$ is a linker, and Ab is an antibody. The conjugate compound provides for complexes of metals such as Tc, Co, Re, Cu, Au and Ag which are useful reagents for in vivo imaging and therapy.

9 Claims, No Drawings

ANTIBODY CONJUGATES WITH MACROCYCLIC LIGANDS

The present application is a file wrapper continuation of U.S. application Ser. No. 07/772,777 filed Oct. 7, 1991, now abandoned; which is a divisional of U.S. application Ser. No. 07/132,955 filed Dec. 14, 1987 which issued to U.S. Pat. No. 5,087,696 on Feb. 11, 1992.

FIELD OF THE INVENTION

This invention relates to a conjugate compound comprising a macrocyclic ligand and an antibody, to a metal complex of the conjugate compound and to formulations of the metal complex for use in therapy and diagnosis.

BACKGROUND TO THE INVENTION

It is known to label an antibody with a metal atom, in order to target the metal atom to a specific tissue type, both in vitro and in vivo. Such labelled antibodies have applications in locating specific tissue types (e.g. employing computer-aided tomographic techniques where the metal atom is in some way detectable) and in the treatment of cell disorders (e.g. treating mammalian tumours where the metal atom is a cytotoxic radionucleide).

Conventionally, the metal atom has been complexed to a conjugate compound comprising a ligand covalently attached to an antibody. The ligand may be, for example, an acyclic chelate such as a substituted diethylenetriaminepentaacetic acid (DTPA) (Gansow O. A. et al, Inorg. Chem., (1986), 25, 2772) or ethylenediaminetetraacetic acid (EDTA) (Meares, C. F. et al, Acc. Chem. Res., (1984), 17, 202). Such acylic complexes however tend to be unstable in vivo either as a result of acid-catalysed decomplexation or competitive chelate binding by $Ca^{2+}$ or $Zn^{2+}$ in serum or as a result of competition from transferrin (Moerlein, S. M. et al, Int. J. Nuc. Med. Biol., (1981), 8, 277). The lack of stability can result in uncomplexed metal atoms in the body which have a cytotoxic effect on healthy tissue or which markedly reduce the signal-to-noise ratio of an imaging technique. The use of macrocyclic ligands in the labelling of antibodies has been suggested in broad terms (Gansow, O. A. et al, Am. Chem. Soc. Symp. Ser., (1984), 241, 215; Published British patent application GB2122641A; Meares, C. F. et al, Anal. Biochem., (1985), 148, 249-253)).

The object of the present invention is to provide improved conjugate compounds involving macrocyclic ligands capable of binding metals to give complexes which are stable, in vivo.

SUMMARY OF THE INVENTION

According to a first aspect of the present invention there is provided a conjugate compound having the following structure:

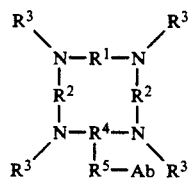
I wherein
$R^1$ is $-(CH_2)_p-R^6-(CH_2)_q-$ where p and q are the same or different and are 0, 1 or 2, and $-R^6-$ is $-(CH_2)_n-$, where n is 0 or 1, $-NH-$, $-O-$, $-S-$ or

, $R^1$ optionally being alkyl substituted, provided that neither p nor q is O unless $R^6$ is $-CH_2-$,
$R^2$ are $-CH_2CH_2-$ or $-CH_2CH_2CH_2-$, optionally alkyl, alkoxyalkyl or hydroxyalkyl substituted,
$R^3$ are the same or different and are $-H$, alkyl, hydroxyalkyl, alkoxyalkyl, carboxyalkyl, carboxyalkyl ester, phosphate, sulphonate or phosphonate
$R^4$ is

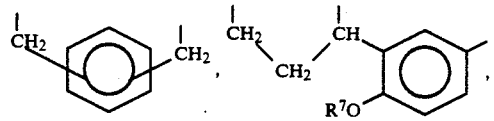

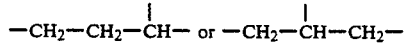

optionally alkyl substituted, wherein $R_7$ is $-H$, alkyl, hydroxyalkyl, or alkoxyalkyl provided that when $R^4$ is $-CH_2-CH-CH_2-$, $R^3$ is not carboxyalkyl,
$R^5$ is a linker, and
Ab is an antibody.

The conjugate compound of the invention provides for complexes of metals or such as Tc, Co, Re, Cu, Au and Ag Pb, Bi, In and Ga which are useful reagents for in vivo imaging and therapy. Particularly preferred are complexes of Tc and Cu.

$R^1$ is preferably $-CH_2CH_2CH_2-$ or $-CH_2CH_2-O-CH_2CH_2-$. The radicals $R^2$ are preferably the same and may be $-CH_2CH_2-$. In each case, one or more hydrogen atoms may be replaced with an alkyl hydroxyalkyl or alkoxyalkyl radical, such as lower alkyl radical, for example methyl.

The aromatic ring, where present, in $R^4$ may be 1,3,5 or 1,3,4 substituted depending to the ring size required and the synthetic route adopted to make the compound.

$R^4$ may be substituted with lower alkyl such as methyl. $R^7$ is preferably $-H$ or lower alkyl ($C_1-C_3$) such as methyl, but may be higher alkyl such as $C_4-C_{15}$ alkyl.

The linker, $R^5$, may be any diradical adapted to link the antibody to the macrocyclic part of the conjugate compound such that the binding affinity and specificity of the antibody are not substantially impaired and such that the macrocyclic part of the conjugate molecule may coordinate with a metal, such as a transition metal or a B-metal.

The antibody, Ab, may be a complete antibody molecule or a fragment thereof or an analogue of either of these, provided the antibody Ab comprises a specific binding region, for example a Fab' or F(ab)$_2$' fragment. The antibody Ab may be a polyclonal or a monoclonal antibody or a fragment thereof. Thus the antibody Ab may be obtained from a hybridoma cell line or other animal cell line. Preferably the antibody Ab has specificity for a mammalian tumour.

In a second aspect of the invention there is provided a conjugate compound of the invention including a complexed metal atom. The metal is preferably a metal selected from Tc, Re, Co, Cu, Au, Ag, Pg, Bi, In and Ga. Particularly preferred are complexes of Tc and Cu. The metal is suitably a radioactive isotope.

The radioisotopes of technetium (Tc) and rhenium (Re) provide useful reagents for imaging and therapy. In particular, $^{99m}$Tc is a strong γ-emitter and, as such is useful in γ-ray imaging. $^{186/188}$Re is a good β-emitter and is useful for β-particle therapy. Both are readily available from a generator as the MO$_4$ anion, and may be complexed in a reduced form to provide complexes which are stable in body fluids.

In a preferred form of the first aspect of the invention there is provided a conjugate compound having the structure:

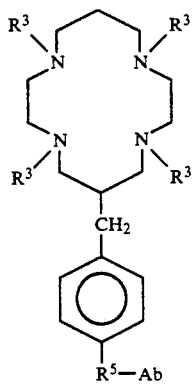

II wherein R$^3$, R$^5$ and Ab are as defined for structure I above R$^3$ is preferably —H.

In a preferred form of the second aspect of the invention there is provided a conjugate compound of structure II complexed with a technetium, copper or rhenium atom, preferably $^{99m}$Tc, $^{67}$Cu, $^{64}$Cu, or $^{186/188}$Re.

In a further preferred form of the first aspect of the invention there is provided a conjugate compound having the structure:

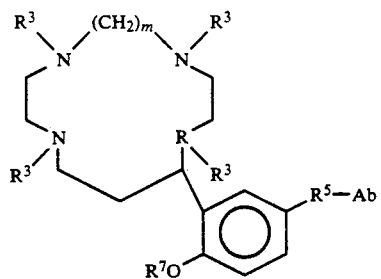

III wherein m is 1 to 5 and R$^3$, R$^5$ and R$^7$ are as defined for structure I above.

The conjugate compound of structure III is suitable for complexing a range of metal atoms, including Tc, Cu, Co, In, Au and Ag, optimum binding being achieved by selection of the ring size by adjustment of parameter m and by adjusting the potential coordination number by choice of radical R$^3$.

In a further preferred second aspect of the invention, there is provided a conjugate compound of structure III wherein m is 3 and R$^3$ is —H or —CH$_3$ complexed with a technetium, rhenium, copper or gold atom, preferably $^{99m}$Tc, $^{67}$Cu, $^{64}$Cu, $^{199}$Au, $^{186/188}$Re.

The conjugate compound of the second aspect of the invention may be used as a pharmaceutical, for example, in the treatment of mammalian tumours or as a diagnostic reagent for use in imaging in vivo as a tracer.

In a third aspect, the invention provides a composition comprising a conjugate compound of the second aspect of the invention or an addition salt thereof and a pharmaceutically acceptable carrier. The composition may be used in the treatment of tumours or as a diagnostic reagent for imaging in vivo.

In a fourth aspect, the invention provides a compound of the following general structure:

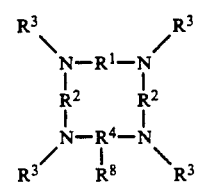

IV wherein R$^1$, R$^2$, R$^3$ and R$^4$ are as defined for structure I above and R$^8$ comprises a reactive group covalently attached to R$^4$. The reactive group provides a point of attachment for an antibody (Ab) either directly, or through a linker. R$^8$ may comprise —(CH$_2$)$_n$—NH$_2$, —(CH$_2$)$_n$—Ar—(CH$_2$)$_m$—NH$_2$, —(CH$_2$)$_n$—CO$_2$H, —(CH$_2$)$_n$—Ar—NCS, or —(CH$_2$)$_n$NHCOR$^9$, wherein n and m=0 to 4 and are the same or different and R$^9$ is a haloalkyl such as —CH$_2$Br. The isothiocyanate and haloalkyl functionalised cycles may be linked directly to an antibody thiol or amino group. Most preferably R$^8$ is a primary amine such as —CH$_2$—Ar—CH$_2$NH$_2$.

It has been discovered that an exocyclic primary amine having a pKa from 8 to 10 exhibits exceptional qualities of selectivity allowing the attachment of linkers to the macrocycles of the invention without substantial disadvantageous side reactions and polymerisation resulting from the existence of the saturated ring nitrogens. The selectivity effect is optimised by careful pH control. Suitably, the attachment of a linker to compound IV is conducted at from pH 6 to pH 8. The primary amine may be conveniently reacted with an acylating agent, such as an activated ester moiety on a linker compound.

The linker comprises a moiety for reaction with R$^8$ and a moiety for attachment to antibody. Suitably the moiety for attachment to antibody is a thiol-specific group such as a maleimide group or a vinyl group conjugated with an aromatic nitrogen heterocycle (e.g. a vinyl pyridine group).

In a preferred aspect of the invention, a primary amine group is covalently linked to a maleimide or vinyl pyridine-containing linker compound, which may be subsequently reacted with a thiol group on the antibody or modified antibody. This compound therefore provides an important intermediate in the production of a conjugate compound according to the first or second aspect of the invention.

The invention further provides addition salts of the conjugate compounds described.

The invention further provides a method for preparing conjugate compounds of the first aspect of the invention comprising reacting together a compound of the fourth aspect of the invention with a linker and an antibody or an antibody fragment.

The invention further provides a method for the treatment of a diseased cell comprising administering an effective amount of a conjugate compound according to the second aspect of the invention, the conjugate compound comprising an antibody having specificity to the diseased cells and the macrocycle including a metal cytotoxic to the diseased cells. The diseased cells may be, for example, mammalian tumour cells.

The invention further provides a method of tumour imaging comprising administering an effective amount of a conjugate compound of the second aspect of the invention, the conjugate compound comprising an antibody to the tissue and the macrocycle including a detectable metal. The tissue may be for example, mammalian tumour cells.

The invention is illustrated by the following Examples.

Description of Specific Embodiments

EXAMPLE 1

A synthesis was performed of a macrocyclic compound having the structure:

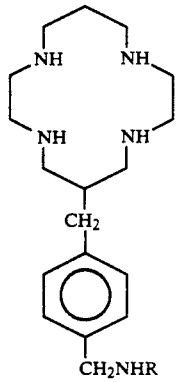

V a) R = —H b) R = —COCH$_2$OCH$_2$— 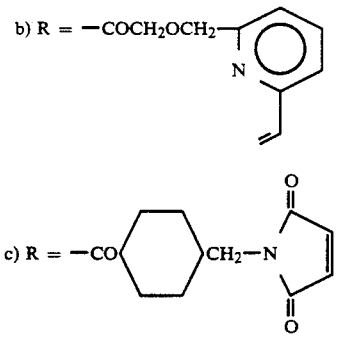

c) R = —CO⟨⟩CH$_2$—N

To a solution of sodium ethoxide (0.051M) in dry ethanol (100 cm$^3$) under nitrogen, was added diethyl malonate (16 g, 100 mmol) in dry ethanol (35 cm$^3$) and the mixture was stirred at room temperature (0.5 h). To the cooled solution was added a solution of α-bromo-paratolunitrile (10 g, 0.051 mol) in dimethylformamide (50 cm$^3$) and the mixture was refluxed (24 h). After cooling to room temperature, distilled water ( 150 cm$^3$) was added, the mixture filtered and the filtrate was extracted with di ethyl ether (3×50 cm$^3$). The ether was removed under reduced pressure and the residue distilled to yield p-cyanobenzyldiethylmalonate (6 g, 45%), bp 150° . (0.01 mm) ($\delta_H$CDCl$_3$) 7.59(2H, d, Hr); 7.33 (2H d, Ar); 4.16 (4H, mult, CH$_2$O) 3.63 (1H,t, CHCH$_2$), 3.27 (2H, d, CHCH$_2$); 1.22 (6H, t, CH$_3$). ($\delta_c$ CDCl$_3$) 167.3(COEt); 143.3, 132.1, 129.5, 116.5(Ar); 110.5 (CN); 61.6 (CH$_2$O); 53.0 (CO$_2$Et)$_2$); 34.4 (CH$_2$—Ar); 13.8(CH$_3$).

A mixture of 1,3,8,11-tetraazaundecane (2.77 g, 17.3 mmol) and p-cyanobenzyldiethylmalonate (4.75 g, 17.3 mmol) in dry ethanol (50 cm$^3$) was refluxed for five days, evaporated to dryness and the residue chromatographed on silica gel (0.063 0.20 mm, Merck) gradient eluting with an aqueous ammonia/methanol dichloromethane solvent of composition which was initially 1:12:87 and finally 6:44:50. The required diamide was isolated as a colourless solid (1.1 g, 19%), mp 209°–211° C. ($\delta_H$ CDCl$_3$) 7.56 (2H,d,Ar), 7.33 (2H,d,ArH), 6.65 ( 2H, brs, NHCO), 3.50 (2H, mult, CH$_2$Ar), 3.25 (4H, mult., CH$_2$NCO), 1.78 (2H, brs, NH), 1.65 (2Y, mult., CH$_2$C) m/e (isobutane DCI) 344 (m+ =1) IR (KBr) $\nu$ 3290 (NH), 2910, 2805, (CH), 2225 (C=N), 1638(NCO), 1530 (NH) Rf(SiO$_2$: aq.NH$_3$/MeOH/CH$_2$Cl$_2$) (6:44:50) 0.25.

To the diamide (0.97 g, 2.8 mmol) in tetrahydrofuran (25 cm$^3$) was added by syringe under nitrogen a borane-tetrahydrofuran solution (47 cm$^3$, 1.0M) and the mixture refluxed (24 h). After destroying the excess borane by careful addition of methanol (4 cm$^3$), the solution was evaporated to dryness and the residue treated with hydrochloric acid (6M, 30 cm$^3$) and refluxed for 3h. On cooling, the solution was basified with sodium hydroxide (2.5 cm$^3$) and extracted with chloroform (3×50 cm$^3$). Removal of solvents under reduced pressure gave a colourless residue which was recrystalised from toluene to give the desired pentamine (Va) as a colourless solid (0.75 g, 83%), mp 149°–150° C. ($\delta_H$ CDCl$_3$) 7.21 (2H,d,ArH), 7.14(2H,d,ArH), 3.83(2H,d,CH$_2$Ar) 2.8 2.4(19H, mult., CH$_2$Ar+ CH$_2$N), 2.2 (6H,brs,NH), 1.71 (2H,quint, CH$_2$C) m/e (isobutane DCI) 320 (m+ =1), 319 (M+) ($\delta_c$ CDCl$_3$) 140.9 (ArCH$_2$-C aryl) 139.0 (CH$_2$-C(aryl); 129.1, 127.0 (rCH); 55.8, 50.72, 49.3 46.1 (CH$_2$N); 40.8 (C, 38.6 CH$_2$-Ar); 29.3 (CH$_2$).

To solution of the p-nitrophenyl ester of 2-vinyl, 6-methoxy acetic acid pyridine (31.2 mg. 0.1 mmol) in p-dioxan (5 cm$^3$) was added a solution of Va (31.9 mg, 0.1 mmol) in buffered water (pH 6.8, 5 cm) 0.5M in 1,4-piperazine bis (ethanesulphinic acid) [PIPES]) and the; solution stirred at 20° C. for 3 r. Purification of the ester by ion-exchange HPLC gave the desired ester Vb (44.5 mg, 90%). m/e (fast atom bombardment, glycerol/H$_2$O) 495 (M+1), 494.33 (m+), 304, 224, 185, 115. ($\delta_H$D$_2$O as the diacetate salt) 7.76 (1H,t,pyCH,J 8.Hz$_2$); 7.48 (1H,d,pyCH); 7.30 (1H,d,pyCH); 7.17 (3H,brs,ArCH); 6.74 (1H,d,vinylCH); 6.03(1H,d,J 17.7); 5.50 (1H,d,J 11.0); 4.64 (2Y, COCH$_2$O); 4.33 (2H$_3$S$_3$ CH$_2$O); .15 (2H,S, CH$_2$NH); 2.98–2.32 (19Y, mult. CH$_2$N+CH$_2$Ar+CHCH$_2$), 1.84 (2Y, mult, CH$_2$CH$_2$CH$_2$).

The maleimide fuctionalised macrocyle Vc may be made in a similar manner to that described for Vb, using the p-nitrophenyl or N-hydroxysuccinimide ester of N-(4-carboxycyclohexylemthl)-malemide, (Yamada, et al, Eur. J. Biochem, (1979), 101, 395).

In order to link the functionalised macrocycle to the antibody, the antibody was first reacted with Traut's reagent (2-iminotheiolane) to give free thiol groups for attachment. For example, a solution of Lym-1 (2 mg) in 0.2M sodium phosphate buffer (pH 7.4) was mixed with 75 μdm³ of 2-iminothiolane (20 mM) in 50 mM triethanolamine-HCl (pH 8) and B-thioethanol (6 μdm³) was added. After incubating at 4° C. (1h), the modified antibody was purified on a G-10 Sepharose column. To a solution of the antibody at pH 6.8 (PIPES buffer) was added the vinyl-pyridine conjugated macrocycle, (Vb), and the reaction was allowed to proceed for 3 hours at room temperature. The resulting macrocycle-linker-antibody conjugate was purified on a G-10 Sepharose column.

Complexation of Vb or Vc with technetium was effected using modifications of the reported literature methods (Troutner el al Int. J. Appl. Radiat Isot. (1982), 33,891; Childs R. L. et al, U. Nucl. Med., (1985), 26, 193) using $TcO_4^-$ in the presence of stannous tartrate and using a phosphate or succinate buffer, in order to facilitate transfer of $^{99m}Tc$ from reduced technetium (V) to the macrocycle.

Complexation of rhenium was achieved by reaction of equimolar quantities of Vb and $ReOCl_3 (PPH_3)_2$ (Johnson et al, J. Chem. Soc., (1964), 1054) in chloroform.; After 5 min. at 25° C., diethylether was added and a $ReOCl(Vb)^{2+}$ complex precipitated. In aqueous solution this exists primarily as the $ReO_2(Vb)^+$ complex, as the chlorine trans to the Re-oxo bond is labile.

A solution of $^{64}CuCl_2$ (30 μl), was added to the macrocycle conjugate [200 μl with approx. 3 mg Ab/ml] in 0.1M sodium acetate or 0.1M sodium succinate at a pH of 6.0. The solution was incubated at 35° C. for 0.5 y, and then chromatographed on a Sephadex G-50 (fine) gel column [which had been previously swollen (overnight) in the PBS buffer used for protein eluting] of dimension 1 cm×6 cm, collecting 0.5 ml aliquots and counting each fraction in order to separate the desired copper-bound antibody macrocycle complex.

EXAMPLE 2

A synthesis was performed of a macrocyclic compound having the structure:

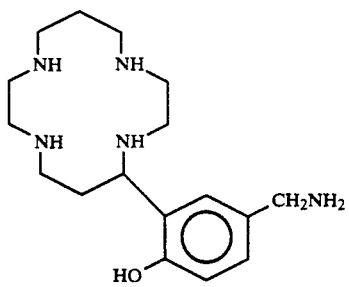

VI

6- Cyanocoumarin (3.46 g, 20 mmol), prepared from 6-aminocoumarin via diazotisation followed by reaction with cuprous cyanide (Morgan E. T., et al, J. Chem. Soc. (1904), 1230), was added to a solution of 1,9-diamino-3, 7-diazononane (3.20 g, 20 mmol) in methanol (200 cm³) and the mixture was refluxed under argon for 6 days following the method of Kimura (J. Chem. Soc. Commun. (1985), 335). After evaporation of the methanol, the residue was chromatographed on silica as described in Example 1, and the resultant amide was reduced using excess borane-tetrahydrofuran to give VI which was purified by recrystallisation from hot toluene, or using reverse phase HPLC methods.

The macrocycle was linked to a maleimide or a vinylpyridine linker as described in Example 1, and the functionalised macrocycle linked to an antibody Fab' or F(ab)₂' fragment as described above. Complexation of technetium or rhenium s(V) was achieved under reducing conditions from the corresponding salt, using the methods disclosed in Example 1.

EXAMPLE 2

A synthesis was performed of a macrocyclic compound having the structure:

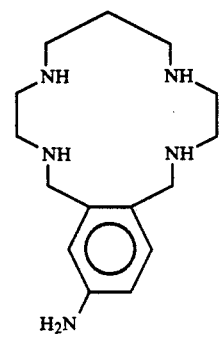

VII

Sodium metal (115 mg, 5 mmol) was dissolved in dry methanol (100 cm³) and N, N¹-3,7-tetra(p-toluenesulphonyl)3,7-diazanonane-1,9 diamine (1.95 g, 2.51 mmol) was added as a solid. The mixture was refluxed under nitrogen for 1 hours, and solvent was removed to yield a solid disodium salt. After removing traces of methanol in vacuo, the solid was dissolved in dry dimethylformamide (50 cm³) and the solution was heated to 80° C. A solution of 6,6-dibromemethyl-3-nitrobenzine (747 mg, 2.5 mmol) in dimethylformamide (20 cm³) was added over a period of 1 hour. After stirring for 2 hours at 80° C. water (40 cm³) was added over a period of 15 minutes and the mixture was stirred for 16 hours at 20° C. The resulting oily product was separated, dissolved in dichloromethane (50 cm³), washed with water (3×15 cm³) and the solvent was evaporated. The cyclic tetratosylate was purified by precipitation from $CH_2Cl_2$hexane (1:4 v/v) and subsequently by chromatography on a neutral column eluting with dichloromethane/methanol, (1%), to yield a tosylated macrocycle as a colourless glass. Detosylation was effected by adding phenol (2 g) and hydrogen bromide in acetic acid (45%, 100 cm³) to the macrocycle and stirring for 24 hours at 80° C. The resulting mixture was cooled and the solvent was removed under reduced pressure, adding toluene to assist the removal of the acetic acid. The residue was dissolved in water (100 cm³) and washed with dichloromethane (4×50 cm³). The aqueous phase was evaporated and the product was redissolved in water (100 cm³) and passed down an anion exchange resin (OH⁻form, Amberlite IR400). the aqueous solution thus obtained was evaporated, leaving a product which was crystallised as the hydrochloride salt form ethanol/hydrochloric acid. The amine was regenerated by passage through an anion exchange column, and is a pale yellow oil. Reduction of the aromatic nitro group to the corresponding amino group was effected by dissolving the free amine (618 mg, 2 mmol) in ethanol, adding palladium on carbon (100 mg, 10%) and hydrogenating under 2 atmospheres of 30° C. for 3 hours. After filtering to remove spent catalyst, the solvent was removed to yield compound VI which was stored at −30° C. under nitrogen.

Complexation of Re was achieved as described in Example 1.

EXAMPLE 4

A synthesis was performed of a macrocyclic compound having the structure:

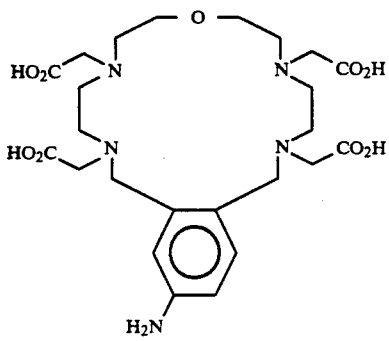

VIII

The synthesis was essentially as for macrocyclic compound VII described in Example 3, except that the disodium salt of $N,N^1$-3,9-tetra(p-toluenesulphonyl)-6-oxa- 3,9-diazadecane-1,11-diamine was used (Dietrich, M. W. et al, Helv. Chim. Acta, (1983), 66, 1262) and acetate side chains were added to the ring nitrogen atoms of the free amine prior to reduction of the aromatic nitro group.

Sodium hydroxide (1.4 g, 37.5 mmol) in water (10 cm$^3$) was added to bromoacetic acid (2.42 g, 17.5 mmol) in water (10 cm$^3$) at below 5° C. The free amine in ethanol (10 cm$^3$) was added and the temperature was held at 70° C. for 2 hours. After cooling, the solution was brought to about pH 3.5 with hydrochloric acid, when a white precipitate of the substituted macrocycle VIII was formed. This was filtered, recrystallised from water and dried in a vacuum.

Complexation with $Pb^{2+}$ was effected under aqueous conditions by mixing equimolar concentrations of lead nitrate and the macrocyle.

EXAMPLE 5

A synthesis was performed of a macrocyclic compound having the structure:

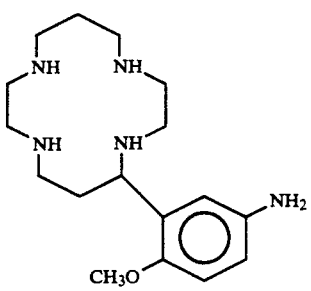

IX

EXAMPLE 5

A synthesis was performed of a macrocyclic compound having the structure:

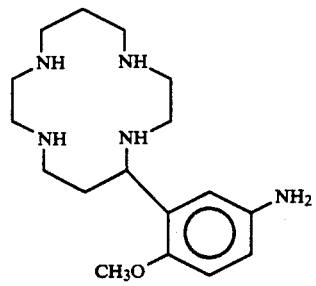

IX 6-nitrocoumarin (9.55 g, 50 mmol) was added to a solution 1,9-diamino-3,7-diazanonane (8 g, 50 mmol) in methanol (200 cm$^3$) under argon, and the mixture was refluxed for 6 days. After evaporation of the methanol, the residue was chromatographed on silica, eluted with $CH_2Cl_2/CH_3OH/NH_4OH$ (70:27:3 v/v) to yield a yellow oil which was further purified by recrystallisation from ethanol/hydrochloric acid to give a trihydrochloride salt of the cyclic amide. Successive reduction of the amide with borane-dimethylsulphide, O-methylation of the phenolic —OH group (under nitrogen) and reduction of the aromatic nitro group using palladium on carbon as described in Example 3 above resulted in macrocycle IX.

Complexation of technetium was effected using techniques known in the literature employing $(NH_4)TcO_4$ and the macrocycle in the presence of $Na_2S_2O_4$ or stannous tartrate.

EXAMPLE 6

A synthesis was performed of a macrocyclic compound having the structure:

X

The synthesis was essentially as for macrocyclic compound IX except that acetate side claims were added to the ring nitrogen atoms, as described in Example 4, prior to reduction of the aromatic nitro group.

Complexation of indium and gallium is effected by reaction of the macrocycle in water with $InCl_3$ or $GaCl_3$ solution in 0.04M HCl under controlled pH using acetate or citrate buffer for 45 minutes (see for example Buckley, R. G. et al, Febs. Lett., (1984), 166, 202 and Meares, C. F. et al, J. Protein, Chem., (1984), 3, 215).

The macrocycle produced in Example 1, 2, 3 or 4 may be covalently bound to an antibody or an antibody fragment, using standard techniques, before or after complexation with the metal. For example a Fab'-linker macrocycle conjugate according to the present invention may be prepared substantially as described below for the model macrocyle, 14-(5-aminophenyl)-1, 4, 8, 11-tetraazocyclotetradecane. 14-(5-aminophenyl)-1, 4, 8, 11-tetraazocyclotetra decane (1m mole) was dissolved in 0.2M phosphate buffer (pH 7.4) and treated with the heterobifunctional cross-linking reagent succinimidyl-4-(p-maleimidophenyl) butyrate (1m mole) dissolved in 0.2M phosphate buffer (pH 7.4), for two hours at room temperature. The resulting macrocycle-linker was purified using silica gel column chromatography, substantially as decribed by Kimura et al, (Jnl. Chem. Cos. Chem. Comm., (1985), p 385).

A monoclonal antibody was treated with the enzyme pepsin to generate a F(ab')$_2$ fragment. The f(ab')$_2$ fragment was then purified using gel permeation chromatography. The purified F(ab')$_2$ fragment was then treated with the reducing agent dithiothreitol (1m M) at pH 8 for three hours at room temperature. The resulting Fab' fragments were then acidifed and passed through a G.10 Sepharose column to yield pure Fab' fragments. The resulting Fab' (0.1m mole) was then dissolved in 0.2M phosphate buffer (pH 7.4) and added to a solution of the macrocycle-linker conjugate (1m mole) in 0.2M phosphate buffer (pH 7.4).

The Fab' fragment and macrocycle-linker conjugate were then allowed to react for three hours under argon at room temperature and the resulting macrocycle-liner-Fab' conjugate purified on a G.10 Sepharose column.

It will be understood that the invention is described by way of Example only and modifications of detail may be made within the scope of the invention.

What is claimed is:

1. A conjugate of a monoclonal or polyclonal antibody or antigen binding fragment thereof covalently bound, either directly or through a divalent linking group, to a macrocyclic ligand of the formula:

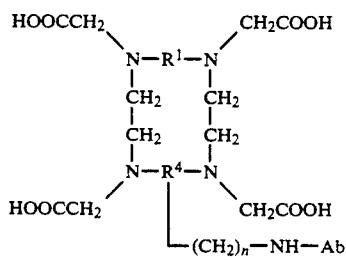

wherein
n has a value of from 0 to 4;
R$^1$ is —CH$_2$—CH$_2$—CH$_2$— or —CH$_2$—CH$_2$—O—CH$_2$—CH$_2$—; and
R$^4$ is

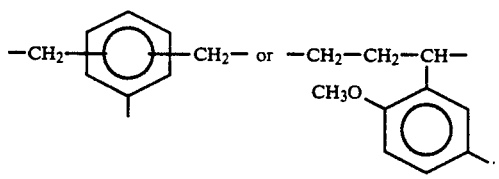

Ab is a monoclonal or polyclonal antibody or antigen binding fragment thereof.

2. A conjugate according to claim 1 wherein said macrocyclic ligand has the formula:

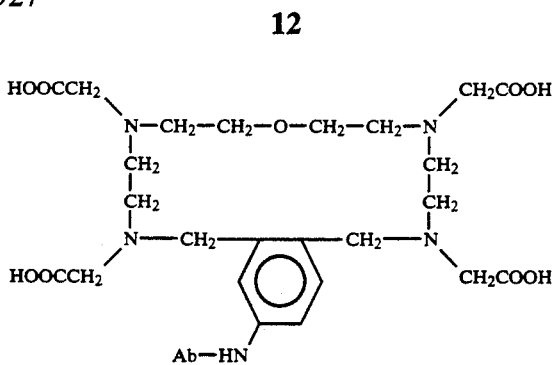

3. A conjugate according to claim 1 wherein said macrocyclic ligand has the formula:

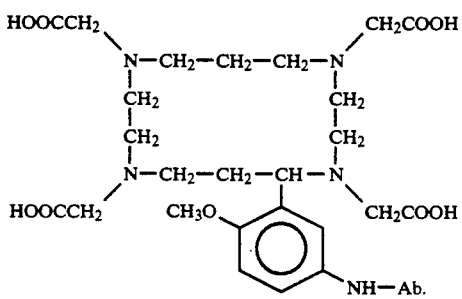

4. A complex of a conjugate according to claim 1 with a metal atom.

5. A complex according to claim 4 wherein the metal atom is selected from the group consisting of technectium, rhenium, cobalt, copper, gold, and silver.

6. A composition comprising a member selected from the group consisting of a conjugate according to claim 1 and a complex thereof with a metal atom in combination with a pharmaceutically acceptable carrier.

7. A coupling agent of the formula:

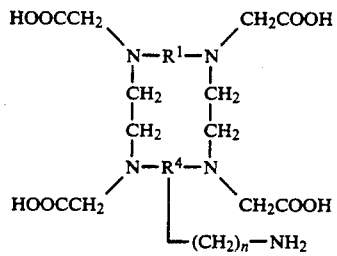

wherein
n has a value of from 0 to 4;
R$^1$ is —CH$_2$—CH$_2$—CH$_2$— or —CH$_2$—CH$_2$—O—CH$_2$—CH$_2$—; and
R$^4$ is

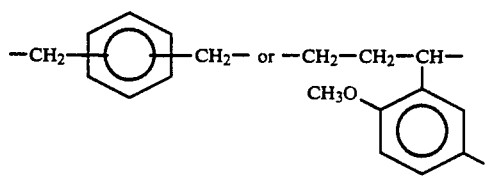

8. A coupling agent according to claim 7 having the formula:

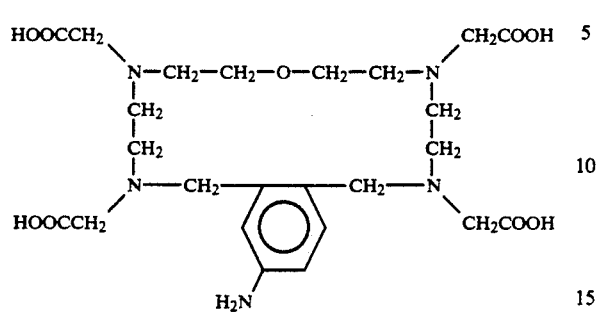
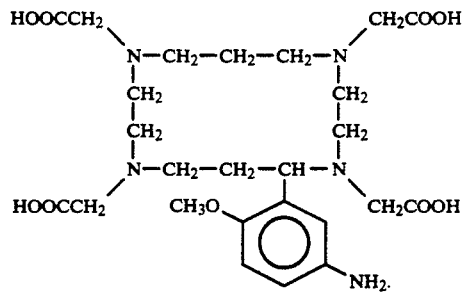
9. A coupling agent according to claim 7 having the formula:
* * * * *